(12) United States Patent
Guichou et al.

(10) Patent No.: US 11,638,417 B2
(45) Date of Patent: May 2, 2023

(54) COMPOSITION COMPRISING ARTHROPODS AND ASTIGMATID MITE EGGS

(71) Applicants: Bioline Agrosciences France, Paris (FR); Centre International D'Etudes Superieures en Sciences Agronomiques, Montpellier (FR)

(72) Inventors: Sabine Guichou, Clapiers (FR); Serge Kreiter, Lauret (FR); Maxime Ferrero, Bar Sur Loup (FR); Pascal Maignet, Saint Vallier De Thiey (FR)

(73) Assignees: Bioline Agrosciences France, Paris (FR); Centre International D'Etudes Supérieures en Sciences Agronomiques, Montpellier (FR)

( * ) Notice: Subject to any disclaimer, the term of this patent is extended or adjusted under 35 U.S.C. 154(b) by 157 days.

(21) Appl. No.: 17/038,550

(22) Filed: Sep. 30, 2020

(65) Prior Publication Data

US 2021/0007336 A1 Jan. 14, 2021

Related U.S. Application Data

(63) Continuation of application No. 14/410,272, filed as application No. PCT/EP2013/063130 on Jun. 24, 2013, now Pat. No. 10,966,413.

(30) Foreign Application Priority Data

Jun. 22, 2012 (FR) ...................................... 1255950

(51) Int. Cl.
*A61K 35/64* (2015.01)
*A01K 67/033* (2006.01)
*A01N 63/14* (2020.01)
*A01N 63/16* (2020.01)

(52) U.S. Cl.
CPC ............ *A01K 67/033* (2013.01); *A01N 63/14* (2020.01); *A01N 63/16* (2020.01)

(58) Field of Classification Search
None
See application file for complete search history.

(56) References Cited

U.S. PATENT DOCUMENTS

2009/0205057 A1* 8/2009 Bolckmans .......... A01K 67/033 800/8

FOREIGN PATENT DOCUMENTS

| | | | |
|---|---|---|---|
| CN | 101040612 A | 9/2007 | |
| CN | 101288392 A | 10/2008 | |
| CN | 101322483 A | 12/2008 | |
| EP | 2248417 A2 | 11/2010 | |
| EP | 2380436 A1 | 10/2011 | |
| EP | 2612551 A1 * | 7/2013 | .......... A01K 67/033 |
| FR | 1255950 A | 3/1961 | |
| GB | 2393890 A | 4/2004 | |
| WO | 2006057552 A1 | 6/2006 | |
| WO | 2006071107 A1 | 7/2006 | |
| WO | 2007/075081 A1 | 7/2007 | |
| WO | 2008015393 A2 | 2/2008 | |
| WO | WO-2008015393 A2 * | 2/2008 | .......... A01K 67/033 |
| WO | 2008/104807 A2 | 9/2008 | |

OTHER PUBLICATIONS

Honda et al. (1998) Appl. Entomology Zool. 33(3): 449-453. (Year: 1998).*
Momen (2011) Acta Phytopathologica et Entomologica Hungerica 46(2): pp. 267-275. (Year: 2011).*
Vantornhout et al. (2005) Experimental and Applied Acarology 35: 185-195. (Year: 2005).*
Sep. 18, 2013—(PCT) International Search Report—App PCT/EP/2013/063130.
Database WPI, Week 200914; Thomson Scientific, London, GB; AN 2009-A98911; XP002690250 & CN 101 288 392 A (Zhang Y), Oct. 22, 2008 (Oct. 22, 2008), abstract.
Database WPI, Week 200918; Thomson Scientific, London, GB; AN 2009-B47930; XP002690251 & CN 101 322 483 A (Lai Y), Dec. 17, 2008 (Dec. 17, 2008), abstract.
Gilkeson L A: "Mass Rearing of Phytoseiid Mires for Testing and Commercial Application", Advances In Insect Rearing for Research, Jan. 1, 1992 (Jan. 1, 1992), pp. 489-506, p. 495, paragraph 3; p. 496, paragraph 1; XP003002501.
Shih C I T: "Automatic Mass-Rearing of Amblyseius Womersleyi (Acari: Phytoseiidae)", Experimental and Applied Acarology, Chapman & Hall, GB, vol. 25, No. 5, Jan. 1, 2001 (Jan. 1, 2001), pp. 425-440, XP009050379, ISSN D168-8162, DOI: 10.1023/A: 1017978017990, abstract.
McMurthy J A et al: "Nutritional Ecology of Phytoseiid Mites", Nutritional Ecology of Insects, Mites, Spiders and Related Invertebrates; Wiley, New York, NY, US; Jan. 1, 1987 (Jan. 1, 1987), pp. 609-644, p. 620, lines 1,9,11; table 19.1; p. 621, lines 17,22; table 19.1; XP008068054.
Zhang Y et al: "Potential of Amblyseius Cucumeris (Acari: phytoseiidae) as a Biocontrol Agent Against Schizotetranychus Nanjingensis in Fujian, China", Systematic and Applied Acarology Special Publication, Systematic and Applied Acarology Society, London, GB; vol. 4, Jan. 1, 2000 (Jan. 1, 2000), pp. 109-124, XP003002569, p. 112, paragraph 2, p. 114; table 1; XP003002569.
Castagnoli M et al: "Effect of Long-Term Feeding History on Functional and Numerical Response of Neoseiulus Dalifomicus (Acari: Phytoseiidae)", Experimental and Applied Acarology, Kluwer Academic Publishers, DO; vol. 23, Jan. 1, 1999 (Jan. 1, 199); pp. 217-234; XP003014949; ISSN: 1572-9702; DOI: 10.1023/A: 1006066930637; abstract.

(Continued)

*Primary Examiner* — Russell G Fiebig
(74) *Attorney, Agent, or Firm* — Banner & Witcoff, Ltd.

(57) ABSTRACT

The present invention relates to a biological control composition comprising at least arthropod biological control agents and astigmatid mite eggs. The invention also relates to the use of astigmatid mite eggs as a nutrient source for arthropod biological control agents. The invention also relates to a biological control composition comprising at least one population of arthropod biological control agents, a nutrient source comprising astigmatid mite eggs, and optionally, a support and/or dissemination substrate. Finally, the present invention further relates to a method for rearing arthropods from astigmatid mite eggs as a nutrient source.

9 Claims, 3 Drawing Sheets

(56) References Cited

OTHER PUBLICATIONS

Castagnoli M et al: "Short-Term Changes in Consumption and Oviposition Rates of Neoseiulis Californicus Strains (Acari: Phytoseiidae) After a Diet Shift"; Experimental and Applied Acarology; Chapman & Hall, GB; vol. 25, No. 12; Jan. 1, 2001 (Jan. 1, 2001), pp. 969-983; XP009050378; ISSN: 0168-8162; DOI: 10.1023/A: 1020639301898; abstract.

Database WPI; Week 198233; Thomson Scientific, London, GB; AN 1982-69763E; XP002690254 & SU 874 001 B (N Cauc Phytopath); Oct. 25, 1981 (Oct. 25, 1981); abstract.

Islam S Sobhy et al: "Development, Consumption Rates and Reproductive Biology Of Reared on Various Prey" Biocontrol, Kluwer Academic Publishers, DO; vol. 55, No. 6, Jul. 24, 2010 (Jul. 24, 2010); pp. 753-756; XP019858600; ISSN: 1573-8248; DOI 10.1007/S10526-010-9304-Z; Abstract.

W. Block et al., "Respiration studies on the Antarctic collembolan Cryptopygus antarctius," OIKOS 26: 15-25, Copenhagen 1975, pp. 15-25.

Ewa Szlendak et al., "Energy budget of the grain mite, *Acarus siro* (Acari: Acaridae)," Experimental & Applied Acarology, 10 (1991) 221-230.

D.J. Thurling., "Metobolic Rate and Life Stage of the Mites Tetranychus cinnabarinus Boisd. (Prostigmata) and Phytoseiulus persimilis A-H (Mesostigmata)," Oecologia (Berl.) 46, 391-396 (1980).

William Block., "Oxygen Consumption of the Terrestrial Mite Alaskozetes Antarcticus (Acari: Cryptostigmata)," J. exp. Biol. (1977), 68, 69-87 with 6 figures.

Maria Nomikou et al., "Phytoseiid predators suppress populations of Bemisia tabaci on cucumber plants with alternative food," Experimental and Applied Acarology 27: 57-68, 2002.

Burger et al. "Host feeding in insect parasitoids: why destructively feed upon a host that excretes an alternative?". The Netherlands Entomological Society. Entomologia Experimentalis et Applicata 112: 207-215, 2004.

Internet Publication. Featured Creatures. Entomology & Nematology, FDACS/DPI, EDIS, UF|IFAS. ladybirds, lady beetles, ladybugs (of Florida), scientific name: (insecta: Coleoptera: Coccinellidae). Downloaded at <http://entnemdept.ufl.edu/creatures/beneficial/lady_beetles.htm >.

Quiroz-Marti Nez et al. "Aquatic Insect as Predators of Mosquito Larvae". AMCA Bulletin No. 7. vol. 23(sp2), pp. 110-117.

Blackwood et al. "Prey-Stage Preference in Generalist and Specialist Phytoseiid Mites (Acari: Phytoseiidae) When Offered Tetranychus urticae (Acari: Tetranychidae) Eggs and Larvae". Environmental Entomology 30(6):1103-1111.

C.I.T. Shih. "Automatic mass-rearing of Amblyseius womersleyi (Acari: Phytoseiidae)". Experimental and Applied Acarology 25:425-440. 2001.

Momen et al. Suitability of the flour moth *Ephestia kuehniella* (Lepidoptera: Pyralidae) for three predatory phytoseiid mites (acari: phytoseiidae) in egypt. (2007) International Journal of Tropical Insect Science 27(02):102-107.

Domingos et al. "Diet-dependent life history, feeding preference and thermal requirements of the predatory mite *Neoseiulus baraki* (Acari: Phytoseiidae)" (2009) Exp Appl Acarol (2010) 50:201-215.

Burnett et al. "Prey consumption in acarine preadtor-prey populations reared in the greenhouse" (1971) Canadian Journal of Zoology, vol. 49 p. 903-913.

\* cited by examiner

Light grey plot: Escape fed with A. ovatus mixture of all stages

Black plot: Escape fed with A. ovatus sub-lethal eggs (A)

(B)

COMPOSITION COMPRISING ARTHROPODS AND ASTIGMATID MITE EGGS

RELATED APPLICATION DATA

This application is a continuation application which claims priority to U.S. patent application Ser. No. 14/410,192, filed on Dec. 22, 2014, which is a National Stage Application under 35 U.S.C. 371 of co-pending PCT application PCT/EP2013/063130 designating the United States and filed Jun. 16, 2013; which claims the benefit of FR application number 1255950 and filed Jun. 22, 2012 each of which are hereby incorporated by reference in their entireties.

The present invention relates to a biological control composition comprising at least arthropod biological control agents and astigmatid mite eggs.

The development of pesticides has greatly expanded agriculture by enabling treatment against a wide variety of pests as well as diseases, with a limited number of molecules. The effects of pesticide products depend primarily on their category: insecticides, acaricides, fungicides, herbicides, nematicides, molluscicides, rodenticides, mole killers.

The use of these products, however, contributes to disequilibrium of the biotope, notably by eliminating certain beneficials and/or by creating resistance phenomena, two factors that contribute to the development of crop-damaging pests and pathogenic agents.

The use of biological control agents constitutes one method for fighting against pests, pathogenic agents or adventitious plants by means of their natural antagonistic organisms, such as phytophagous species (for adventitious plants), parasitoids (for arthropods, etc.), predators (for nematodes, arthropods, vertebrates, mollusks, bats, etc.) or pathogenic agents (for viruses, bacteria, fungi, etc.). The use of these biological control agents also allows a reduction in pesticide use.

The use of arthropods, especially Phytoseiidae, as biological control agents has proven the effectiveness of such an approach. Thus, compositions are found on the market comprising populations of *Amblyseius cucumeris*, a predator of thrips larvae, which is a phytophagous species (Thysanoptera), and bran, thus making it possible to more easily distribute the product in crops. These ingredients can, optionally, be provided in pre-pierced sachets, in order to release the predators in a controlled manner over time. Similarly, the use of *Neoseiulus californicus* as a predator of species of Tetranychidae and of Tarsonemidae, and the use of *Amblyseius swirskii* as a predator of thrips or of Aleyrodidae, is currently common.

With this approach, it is necessary to reintroduce the living biological control agent, in this case the arthropod, in sufficient number to achieve the required effect. As a result, the diet of the biological control agents, in particular the arthropods, is determining critical factor for rearing the biological control agent, or in the preparation of biological control compositions.

A large number of documents describe methods for the mass rearing of biological control agents. Traditionally, biological control agents are raised in the presence of a population of prey as food and then are released into crops. The prey populations used can be prey other than natural prey, for example prey that are easier to raise, if they can act as food for the biological control agents. For example, in the field of the mass rearing of arthropods as biological control agents, GB2393890 discloses that *Amblyseius cucumeris* can use *Tyrophagus putrescentiae, T. tropicus* and *Acarus siro* as substitution prey.

Thus, compositions comprising a population of arthropods, a population of prey, and, optionally, a substrate providing support and nutrients for the population of prey, have already been described.

Nomikou et al. have shown that populations of *Amblyseius swirskii* can grow while having a high predator/prey ratio, if they feed on *Tyrophagus putrescentiae* (Experimental and Applied Acarology 27(1-2), 57-68).

The patent application WO2006/057552 discloses that populations of *Amblyseius swirskii* can be raised using astigmatid mites, in particular belonging to the family Carpoglyphidae, Pyroglyphidae, Glyphagidae or Acaridae, as a food source.

This method poses a certain number of problems, however.

On the one hand, it is first necessary to obtain a population of prey, with all the difficulties related to the rearing thereof. In particular, this prey regularly requires food containing mainly grain and yeast, ingredients likely to allow mold to develop.

On the other hand, it is known that the equilibrium between prey and predator populations, which is critical for obtaining the desired number of predators depends on the initial predator/prey ratio. Although this equilibrium is dynamic, it necessarily involves phases of decrease in the predator population. Too high of a prey rate can have a deleterious effect on the evolution of the predators, then leading to a drastic decrease in the population of predators in the composition.

Moreover, in a number of cases, particularly when the preys are household dust mites, it has been noticed that some species can be phytotoxic. In addition, some of the mites often used to rear phytoseiids, in particular among astigmatid mites, are particularly allergenic for man.

Finally, the existing compositions comprising predators and prey, in particular comprising mites, have a shelf life that is often very short, and last at longest about 3 weeks in the field without deteriorating There is thus still a need for improved nutritional sources that could be used for mass rearing of biological control agents, in particular arthropods. More specifically, there is a need for nutritional sources that have an improved shelf life and can therefore improve the overall shelf life of biological control agents compositions.

The inventors have discovered that the use of astigmatid mite eggs to feed populations of arthropods makes it possible to solve the problems of the prior art.

The inventors have more particularly discovered that the specific use of astigmatid mite eggs to feed populations of arthropods is more effective than the use of whole populations of astigmatid mites which further comprise larvae, nymphs and adult astigmatid mites.

In addition, the inventors have discovered that astigmatid mite eggs have a shelf life at room temperature that is longer than other types of arthropod food, about 4 to 6 weeks. Thus, compositions comprising astigmatid mite eggs have a longer shelf life in the field than compositions of the prior art, which comprise other types of foods.

Finally, the inventors have surprisingly discovered that astigmatid mite eggs can be treated in order to prevent them from hatching. The inventors have indeed found that eggs that are treated in a specific way enter a stage wherein they cannot further hatch yet retain a metabolic activity. This stage is herein called sub-lethal stage. Those eggs are particularly advantageous as they have an improved shelf life, and do not deteriorate as fast as eggs treated in different conditions. Moreover, those sub-lethal eggs will not develop in larva and other stages that are not as effective in feeding populations of arthropods.

A first object of the invention is the use of astigmatid mite eggs as a nutrient source for arthropod biological control agents.

A second object of the invention is a biological control composition comprising:
at least one population of arthropod biological control agents,
a nutrient source comprising astigmatid mite eggs, and optionally, a support and/or dissemination substrate.

Another object of the invention is a biological control composition comprising:
at least one population of arthropod biological control agents, a nutrient source comprising at least one astigmatid mite population, and optionally, a support and/or dissemination substrate.

Further, the present invention has for object a method for rearing arthropod biological control agents from astigmatid mite eggs as a nutrient source.

Finally, the present invention has for object a method for rearing arthropod biological control agents from a nutrient source comprising at least one astigmatid mite population.

In the context of the invention, the expression "population of arthropod biological control agents" refers to any population comprising at least two living individuals belonging to at least one of the species of arthropods among the biological control agents. Said population can be comprised of individuals belonging to only one or to several developmental stages of the biological control agent. For example, the population can comprise eggs, larvae, nymphs, adult individuals or mixtures of these various stages. The arthropods used according to the invention are selected, for example, from the class Arachnida, preferentially from mites (order Acari), or from the class Insecta.

In an embodiment, the mites are selected from the orders Mesostigmata and Trombidiforms.

According to an embodiment, the mites can be selected, for example, from the families of phytoseiids (Phytoseiidae), Macrochelidae or Laelapidae.

Advantageously, the phytoseiids can be selected from the subfamily Amblyseiinae, for example *Amblyseius swirskii, Amblyseius largoensis, Amblyseius andersoni*; or from the genus *Neoseiulus*, for example *Neoseiulus womersleyi, Neoseiulus californicus, Neoseiulus cucumeris, Neoseiulus fallacis, Neoseiulus longispinosus*; or from the genus *Iphiseius*, for example *Iphiseius degenerans*; or from the genus *Amblydromalus*, for example *Amblydromalus lailae, Amblydromalus limonicus* or *Amblydromalus manihoti*; or from the subfamily Typhlodrominae, in particular the genus *Typhlodromips*, for example *Typhlodromips montdorensis*; or from the genus *Euseius*, for example *Euseius ovalis, Euseius scutalis, Euseius finlandicus, Euseius gallicus, Euseius stipulatus, Euseius tularensis, Euseius hibisci*.

Advantageously, the mites of the family Macrochelidae can be selected from *Macrocheles*, for example *Macrocheles robustulus*.

Advantageously, the mites of the family Laelapidae can be selected from *Hypoaspis*, for example *Hypoaspis aculeifer, Hypoaspis miles* or *Hypoaspis scimitus*.

Preferentially, the mites are selected from *Amblyseius swirskii, Neoseiulus cucumeris, Amblyseius largoensis, Neoseiulus californicus, Neoseiulus fallacis, Neoseiulus longispinosus, Amblydromalus lailae, Typhlodromips montdorensis, Euseius ovalis, Euseius scutalis, Euseius hibisci*.

According to a particularly advantageous embodiment of the invention, the mites are the species *Amblyseius swirskii*.

According to an embodiment, the arthropods can be selected from the class Insecta. The insects can be selected from the species of the order Hemiptera, for example family Miridae, genus *Nesidiocoris*, for example *Nesidiocoris tenuis* or *Nesidiocoris* spp., or for example the family Anthocoridae, genus *Orius*, for example *Orius laevigatus, Orius insidiosus, Orius* spp., or finally, for example, the family Lygaeidae, genus *Geocoris*, for example *Geocoris* spp.

The insects can be selected from the species of the order Coleoptera, for example the family Coccinellidae, genus *Cryptolaemus*, for example *Cryptolaemus montrouzieri* or *Cryptolaemus* spp.

The insects can be selected from the species of the order Neuroptera, for example family Chrysopidae, for example genus *Chrysoperla*, for example *Chrysoperla* spp.

In the context of the present invention, the term "egg" refers to eggs that have been collected and not yet hatched. For example, the eggs can be used fresh or after having been preserved by any mode of preservation that allows maintaining all of the eggs' nutritional properties. Preferentially, the eggs are preserved by any mode of preservation that allows maintaining the eggs in their development stage without altering the eggs' ability to then develop.

Further, the eggs can be specifically treated in order to prevent them from hatching by inducing a sub-lethal stage. Thus, by "sub-lethal eggs" it is herein referred to eggs that do not hatch and retain metabolic activity. In order to verify that an egg does not hatch, the person skilled in the art may for example put the egg in normal culture conditions that are appropriate for the development of the egg, and verify that the egg does not develop into larvae, nymph and adult, over time. For example, the skilled person can put the egg at 25° C. and at 75% relative humidity, and verify that the egg does not develop into larvae, nymph and adult over time.

Metabolic activity can be evaluated by any technique known in the field. For example, it has been long known that metabolic activity of acari can be evaluated by measuring their respiratory rates, more precisely by measuring the dioxygen ($O_2$) uptake per individual (Szlendak et al., *Exp Appl Acarol.* 10(3-4):221-30, 1991; Block et al., *J exp Biol* 68:69-87, 1977; Block W, *Oikos* 26:15-25, 1975). This approach has also been used for evaluating the metabolic activity of mite eggs (D. J. Thurling, *Oecologia*, 46:3, 391-396, 1980).

Measuring the dioxygen ($O_2$) per egg can easily be performed using a gas analyzer or using a Cartesian Diver micro-respirometer. Such analysis is a routine practice for the person skilled in the art, and does not require to be further explained herein. The inventors have found that sub-lethal eggs can be obtained by exposing them to UV radiations, or to specific temperature conditions. Thus, in order to obtain sub-lethal eggs, the eggs can be exposed to a temperature between −100° C. and 9° C., advantageously between −80° C. and 5° C., even more advantageously between −30° C. and 5° C.

For example, the eggs after collection undergo a brief heat shock and are then stored at a temperature between about −90° C. and 5° C., advantageously between about −30° C. and 5° C., even more advantageously between about −5° C. and 5° C. Advantageously, the heat shock is carried out at a temperature between about −100° C. and 0° C., preferentially at a temperature between about −100° C. and −10° C.

In addition, the inventors have found that induction of the sub-lethal stage depends both on temperature and exposure time to said temperature. As a general rule, they observed that the lower the temperature is, the shorter the exposure time should be. Indeed, as the inventors have found, if the exposure time is too important, the treatment does not result in sub-lethal eggs, but in dead eggs that tend to collapse with time.

For example, one the one hand, when the astigmatid mite eggs are exposed to a temperature between −10° C. and 9° C., the time of exposure could vary between a few days and a few weeks. On the other hand, when the astigmatid mite eggs are exposed to lower temperatures, such as temperatures between −100° C. and −80° C., the time of exposure should be shortened from a few seconds to a few hours.

The inventors have discovered that, for a given temperature, the necessary and sufficient exposure time to obtain a maximum of sub-lethal eggs can be determined by a specific equation. They have determined specific combinations of temperature and exposure time that can be safely used in order to obtain at least 60% of sub-lethal eggs.

Preferably, the eggs of the invention are exposed to conditions comprised in the list consisting of a temperature comprised between 8° C. and 9° C. for between 7 to 10 weeks, a temperature comprised between 7° C. to −4° C. for between 4 to 6 weeks, a temperature comprised between −5° C. to −14° C. for between 1 to 3 weeks, a temperature comprised between −15° C. to −24° C. for between 2 to 5 days, a temperature comprised between −25° C. to −34° C. for between 12 to 36 hours, a temperature comprised between −35° C. to −54° C. for between 2 to 8 hours, a temperature comprised between −55° C. to −79° C. for between 5 to 60 minutes, a temperature comprised between −80° C. to −100° C. for between 10 seconds to 3 minutes.

Yet preferably, the eggs of the invention are exposed to a temperature comprised between 7° C. to −4° C. for between 4 to 6 weeks. Even more preferably, the eggs of the invention are exposed to a temperature comprised between 4° C. to −2° C. for between 4 to 6 weeks. Advantageously, the eggs of the invention are exposed to a temperature of 0° C. for between 4 to 6 weeks.

The inventors have further determined specific combinations of temperature and exposure time that can be safely used in order to obtain at least 80% of sub-lethal eggs.

Preferably, the eggs of the invention are exposed to conditions comprised in the list consisting of a temperature comprised between 8° C. and 9° C. for 9 weeks, a temperature comprised between 7° C. to −4° C. for 5 weeks, a temperature comprised between −5° C. to −14° C. for 2 weeks, a temperature comprised between −15° C. to −24° C. for between 4 days, a temperature comprised between −25° C. to −34° C. for between 24 hours, a temperature comprised between −35° C. to −54° C. for between 6 hours, a temperature comprised between −55° C. to −79° C. for between 30 minutes, a temperature comprised between −80° C. to −100° C. for between 30 seconds.

Yet preferably, the eggs of the invention are exposed to a temperature comprised between 7° C. to −4° C. for between 5 weeks. Even more preferably, the eggs of the invention are exposed to a temperature comprised between 4° C. to −2° C. for between 5 weeks. Advantageously, the eggs of the invention are exposed to a temperature of 0° C. for between 5 weeks.

According to the invention, the eggs can be whole or fractionated. The eggs can be treated so as to extract particular nutrients.

The eggs can be administered alone or mixed with at least one other substrate. The substrate is selected from substrates containing nutrients. For example, the substrate is selected from cereals, cereal flours, in particular wheat flour or corn flour, yeasts, bran, pollen, fruits, dried fruits, sugar, for example dextrose.

In the context of the invention, the term "nutrient source" refers to any embodiment wherein astigmatid mite eggs are used to feed the biological control agents. The nutrient source of the invention is the sole food or is one of the foods used to feed the biological control agents. Preferably, the nutrient source of the invention is the sole nutrient source of animal origin. According to a particularly preferred embodiment, the nutrient source of the invention is the sole food used to feed the biological control agents.

The nutrient source of the invention comprises at least 10%, 20%, 25%, 30%, 35%, 40%, 45%, 50%, 55%, 60%, 65%, 70%, 75%, 80%, 85%, 90%, 95%, 98%, 100% astigmatid mite eggs by weight in relation to the total weight of the nutrient source. Advantageously, the nutrient source of the invention comprises at least a population of astigmatid mites. According to the invention, the population of astigmatid mites consists in astigmatid mites eggs. Thus, the population of astigmatid mites does not contain larvae, nymphs or adult astigmatid mites Preferentially, the nutrient source of the invention consists in astigmatid mite eggs. Thus, in a preferred embodiment, the nutrient source of the invention does not contain larvae, nymphs or adult astigmatid mites.

According to an embodiment, the term "egg" excludes any other stage: for example, astigmatid mite eggs do not contain larvae, nymphs or adult astigmatid mites.

The astigmatid mite eggs of the invention can be selected from eggs of Pyroglyphidae, Acaridae, Carpoglyphidae or Glyciphagidae.

According to an advantageous embodiment, the astigmatid mite eggs are selected from eggs of at least one species of the family Acaridae, for example at least one species of the genus *Acarus*, for example *Acarus siro, Acarus farris, Acarus immobilis* or *Acarus chaetoxysilos*; or, according to another example, at least one species of the genus *Tyrophagus*, such as *Tyrophagus longior, Tyrophagus similis* or *Tyrophagus putrescentiae*; or even at least one species of the genus *Aleuroglyphus*, such *Aleuroglyphus ovatus*; or at least one species of the genus *Lardoglyphus*, such as *Lardoglyphus konoi*, for example; at least one species of the genus *Caloglyphus*, such *Caloglyphus mycophagus* or *Caloglyphus berlesei*; at least one species of the genus *Suidasia*, such as *Suidasia nesbitti*, for example; at least one species of the genus *Thyreophagus*, such *Thyreophagus entomophagus*; at least one species of the family Carpoglyphidae, such as, for example, at least one species of the genus *Carpoglyphus*, for example *Carpoglyphus lactis, Carpoglyphus munroi*; at least one species of the family Glycyphagidae, such as, for example, at least one species of the genus *Glycyphagus*, such as *Glycyphagus domesticus*; at least one species of the genus *Lepidoglyphus*, such as *Lepidoglyphus destructor*; at least one species of the genus *Blomia*, such as, for example, *Blomia freemani*; at least one species of the family Chortoglyphydae, at least one species of the genus *Chortoglyphus*, for example *Chortoglyphus arcuatus*.

Advantageously, the astigmatid mite eggs are selected from eggs of at least one species of the genus *Aleuroglyphus*. According to a particularly advantageous embodiment, the astigmatid mite eggs are selected from eggs of at least *Aleuroglyphus ovatus*.

According to an embodiment, the nutrient source of the invention comprises Acaridae eggs. According to a preferred embodiment, the nutrient source of the invention comprises *Aleuroglyphus ovatus* eggs.

The inventors further discovered that, surprisingly, mixtures of astigmatid mite eggs and lepidopteran eggs act synergistically, leading to particularly significant arthropod growth.

Thus, another object of the invention is the use of astigmatid mite eggs and lepidopteran eggs as a nutrient source for arthropod biological control agents.

Preferably, the nutrient source of the invention further comprises eggs of at least one lepidopteran species. Preferably, the nutrient source of the invention further comprises at least one lepidopteran population. More preferably said lepidopteran population consists in eggs.

According to an embodiment of the invention, the lepidopteran eggs are selected, for example, from the family Pyralidae, for example *Ephestia kuhniella*, *Ephestia elutella*, *Ephestia cautella*, *Corcyra cephalonica* or *Plodia interpunctella*, or for example from the subfamily Gelechiidae, for example *Sitotroga cerealella*. According to a particularly advantageous embodiment, the lepidopteran eggs are *Ephestia kuhniella* eggs.

Thus, according to a particularly advantageous embodiment of the invention, the composition of the invention comprises at least one population of the arthropod species *Amblyseius swirskii*, *Aleuroglyphus ovatus* eggs and *Ephestia kuhniella* eggs.

Preferably, the nutrient source of the invention further comprises 2%, 5%, 10%, 15%, 20%, 25%, 30%, 35%, 40%, 45%, 50%, 55%, 60%, 65%, 70%, 75%, 80% of lepidopteran eggs by weight in relation to the total weight of the nutrient source.

According to a preferred embodiment of the invention, the nutrient source of the invention is comprised of astigmatid mite eggs and lepidopteran eggs, for example in a ratio of astigmatid mite eggs to lepidopteran eggs of between 1:2 and 2:1 by weight.

According to a preferred embodiment, a nutrient source comprising *Aleuroglyphus ovatus* eggs is used for at least one population of arthropods whose species belongs to the family Phytoseiidae.

According to a preferred embodiment, a nutrient source comprising *Aleuroglyphus ovatus* eggs is used for at least one population of arthropods of the species *Amblyseius swirskii*.

The astigmatid mite eggs can be collected by any method known to persons skilled in the art.

According to an embodiment of the invention, the ratio of the weight of the arthropods to the weight of the eggs is preferentially between 1:1 and 1:50. Advantageously, this ratio can be between 1:2 and 1:10. In a particularly advantageous embodiment, this ratio is between 1:3 and 1:7.

According to an embodiment of the invention, the ratio of the weight of the arthropods to the weight of the astigmatid mite eggs is preferentially between 1:1 and 1:50. Advantageously, this ratio can be between 1:2 and 1:10. In a particularly advantageous embodiment, this ratio is between 1:3 and 1:7.

Thus, according to an embodiment, the invention has as an object a method for rearing arthropods from astigmatid mite eggs, comprising the steps of:
a. collecting astigmatid mite eggs,
b. determining the weight of the astigmatid mite eggs obtained,
c. bringing together a weight of astigmatid mite eggs and a weight of arthropods, characterized in that the ratio of the weight of the arthropods to the weight of the astigmatid mite eggs is between 1:3 and 1:7.

According to a preferred embodiment, the invention has as an object a method for rearing arthropods from astigmatid mite eggs and lepidopteran eggs, comprising the steps of:
a. collecting astigmatid mite eggs and lepidopteran eggs,
b. determining the weight of the astigmatid mite eggs obtained and the weight of the lepidopteran eggs obtained,
c. bringing together a weight of astigmatid mite eggs, a weight of lepidopteran eggs and a weight of arthropods, characterized in that the ratio of the weight of the arthropods to the sum of the weight of the astigmatid mite eggs and the weight of the lepidopteran eggs is between 1:3 and 1:7.

According to an embodiment of the invention, a support or dissemination substrate is added to the mixture comprising the population of arthropod biological control agents and the nutrient source. The support or dissemination substrate is selected from inert substrates, such as, for example, particles of vermiculite, particles of pearlite, or mixtures thereof.

The composition of the invention can further comprise traces of the arthropod rearing medium.

Advantageously, the arthropods are reared at a temperature between 5° C. and 40° C., preferentially between 15° C. and 35° C. In a particularly advantageous manner, the arthropods are reared at a temperature between 20° C. and 30° C.

EXAMPLES

Example 1: Effect of a Diet Consisting in Astigmatid Mite Eggs on Growth and Health of Arthropod Biological Control Agents Eggs of *A. swirskii* were deposited in distinct cells and raised at 25° C., 75% HR (for "relative Humidity") and 16/8 (L/D, for "Light/Dark", indicating the time in hours spent in the referred condition).

The resulting *A. swirskii* populations were fed with one of the two following conditions:
a mixture of all stages of *A. ovatus*,
only *A. ovatus* sub-lethal eggs.

Every 12 hours, the *A. swirskii* individuals that escaped or died were noted, along with their developmental stage.

Figure 1:
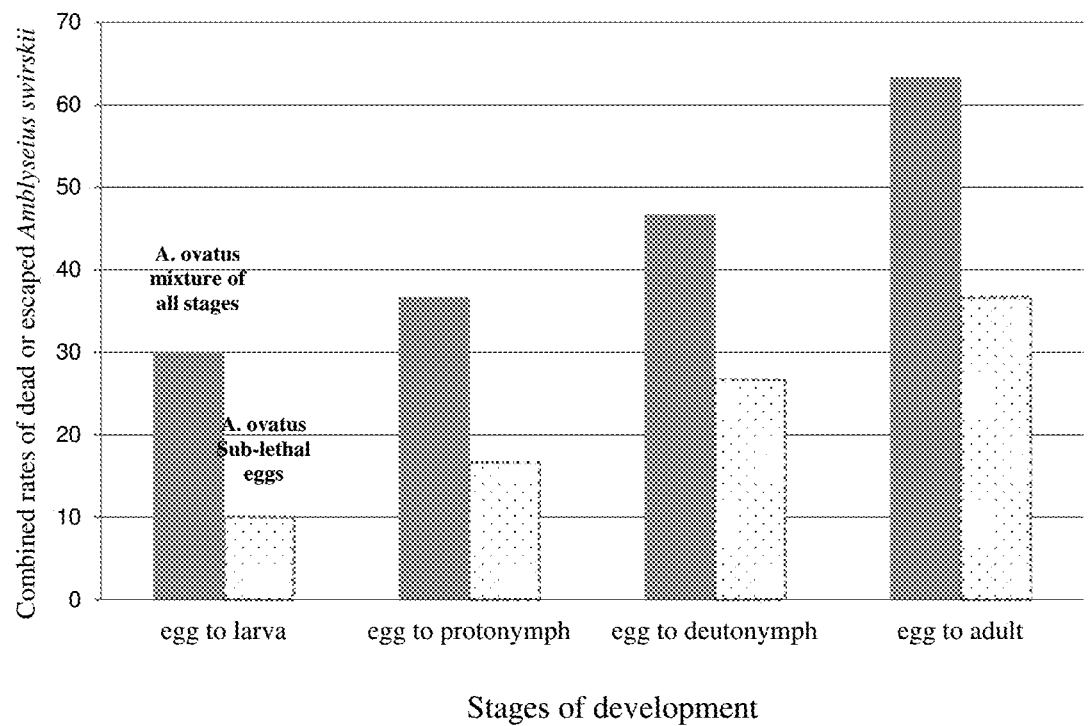
FIG. 1: Combined rates of dead or escaped *Amblyseius swirskii* at different stages of development (in percent of the original population), depending on the food proposed, at 25° C., 75% HR and 16/8 (L/D).

Results are represented FIG. 1.

The combined *A. swirskii* rate of juveniles that died or escaped when only eggs are proposed is lower (37%) than when a mixture of all stages of *A. ovatus* is given to *A. swirskii* (63%).

Conclusion: populations of *Amblyseius swirskii* fed with *Aleuroglyphus ovatus* eggs suffer less death and escapes from individuals than populations of *Amblyseius swirskii* fed with all stages of *Aleuroglyphus ovatus*. Populations of arthropod biological control agents reared on astigmatid mite eggs are likely to be more healthy and numerous than populations of arthropod biological control agents reared on all stages of astigmatid mite.

Example 2: Effect of a Diet Consisting in Astigmatid Mite Eggs on Fecundity of Arthropod Biological Control Agents Young *A. swirskii* females of the same cohort were individually deposited in experimental cells at 25° C., 75% HR and 16/8 (L/D), and a male was given to each female.

The *A. swirskii* females were fed with one of the two following conditions:

a mixture of all stages of *A. ovatus*, only *A. ovatus* sub-lethal eggs.

The fecundity (mean number of eggs/female) of 30 to 60 *A. swirskii* was then noted daily between the first mating and their death.

Figure 2:
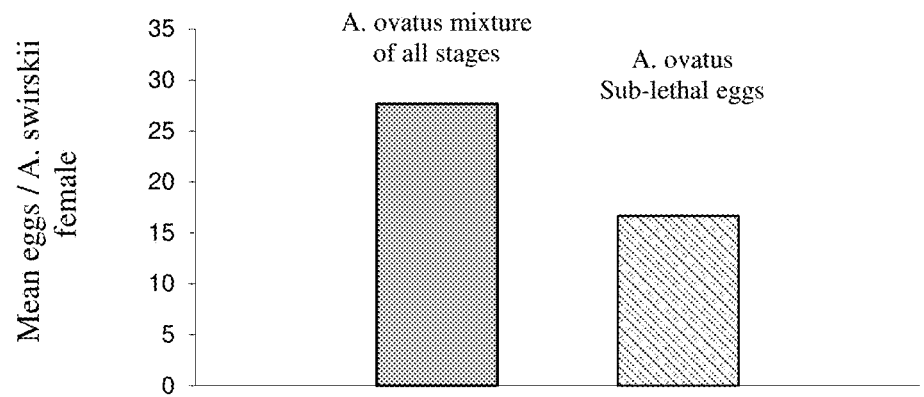
FIG. 2: *Amblyseius swirskii* fecundity depending on the food proposed expressed in eggs per female for the whole adult period at 25° C., 75% HR and 16/8 (L/D).

Results are represented FIG. 2.

Figure 3:
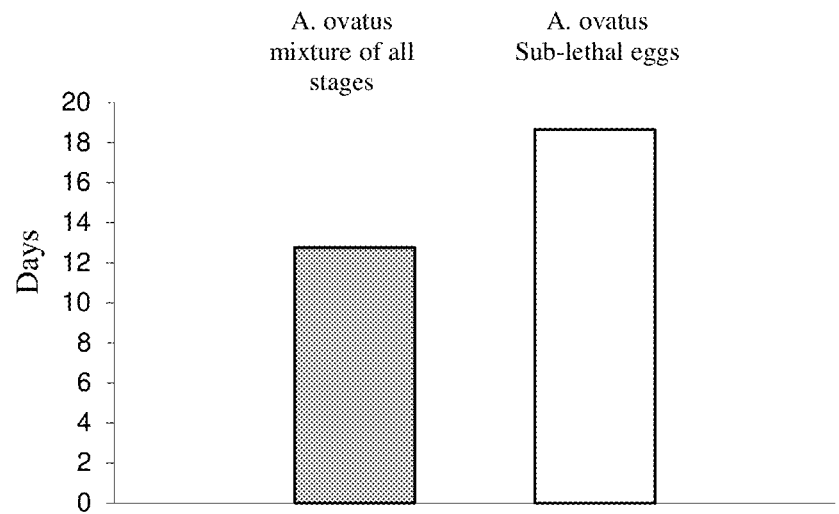
FIG. 3: *Amblyseius swirskii* longevity in days depending on the food given at 25° C., 75% HR and 16/8 (L/D).

The longevity of those females was also noted for the two modalities given above, and is represented FIG. 3.

It appears that when the food given to *A. swirskii* females only consist of sub-lethal eggs, longevity is much higher than when the food is composed of a mixture of all stages of *A. ovatus*. The inverse trend is observed about fecundity for the two modalities tested. No global performance is lost while giving only *A. ovatus* sub-lethal eggs to *A. swirskii*, but an advantage is obtained in term of longevity.

Conclusion: The fecundity of *Amblyseius swirskii* females fed with *Aleuroglyphus ovatus* eggs is more important than the fecundity of the same females fed with all stages of *Aleuroglyphus ovatus*.

The fecundity of arthropod biological control agents reared on astigmatid mite eggs are likely to be more important than the fecundity of arthropod biological control agents reared on all stages of astigmatid mite.

Example 3: Effect of a Diet Consisting in Astigmatid Mite Eggs on Survival of Arthropod Biological Control Agents Young *A. swirskii* females, were maintained at 25° C., 75% HR and 16/8 (L/D).

The *A. swirskii* females were fed with one of the two following conditions for at least 3 days:

a mixture of all stages of *A. ovatus*, only *A. ovatus* sub-lethal eggs.

*Amblyseius swirskii* females were then transferred to individual cells. They were then starved.

Escape was noted daily from the first day of starvation until the end of the experiment.

Figure 4:
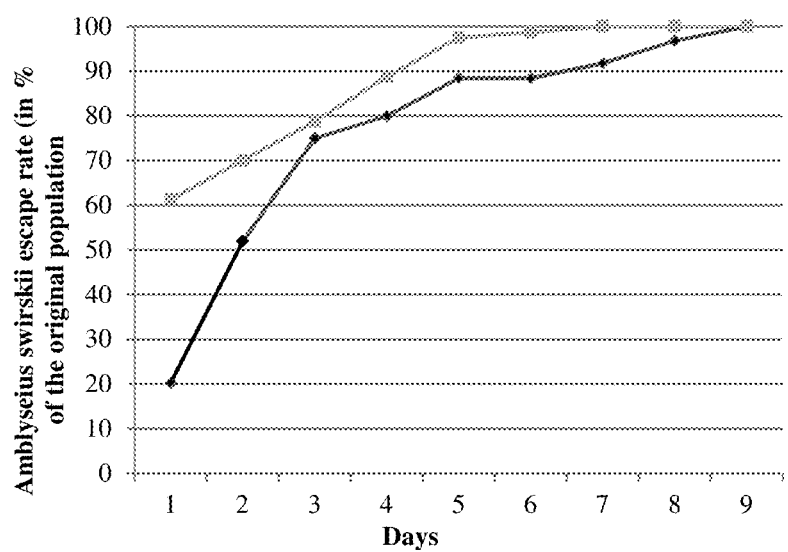
FIG. 4: *Amblyseius swirskii* escape rate (in % of the original population), while submitted to starving, at 25° C., 75% HR and 16/8 (L/D). The populations represented were fed either *A. ovatus* sub-lethal eggs (balck plot), or a mixture of all stages of *A. ovatus* (light grey plot).

Results are represented FIG. 4.

The escape rate was higher when *A. swirskii* were given a mixture of all the stages of *A. ovatus* as food, compared to eggs.

Conclusion: populations of *Amblyseius swirskii* fed with *Aleuroglyphus ovatus* eggs suffer less death and escapes from individuals than populations of *Amblyseius swirskii* fed with all stages of *Aleuroglyphus ovatus*, even after they have been deprived of food. Populations of arthropod biological control agents reared on astigmatid mite eggs are likely to be more healthy and numerous than populations of arthropod biological control agents reared on all stages of astigmatid mite.

Example 4 Sub-Lethal Astigmatid Mite Eggs do not Develop Fungus

A population of *A. ovatus* fed with yeast and wheat bran was prepared. At the end of the preparation, the population of *A. ovatus* contained a mixture of all stages of *A. ovatus*.

A sample of the prepared population was taken, from which eggs were isolated. The isolated eggs where put in a cold storage, in the appropriate conditions to induce a sub-lethal state.

Another sample of the prepared population was taken, and put in a cold storage. This second sample thus contained a mixture of all stages of *A. ovatus*.

After two months, the isolated eggs (A) and the mixture of all stages of *A. ovatus* (B) were taken out of the storage and put back to ambient temperature for a week.

Fungus development was then observed on the sample containing all the stages of *A. ovatus* (B), while no microorganisms' development was observed on the sample containing only sub-lethal eggs (A).

After a week, a picture was taken to illustrate the evolution of both samples.

Figure 5:
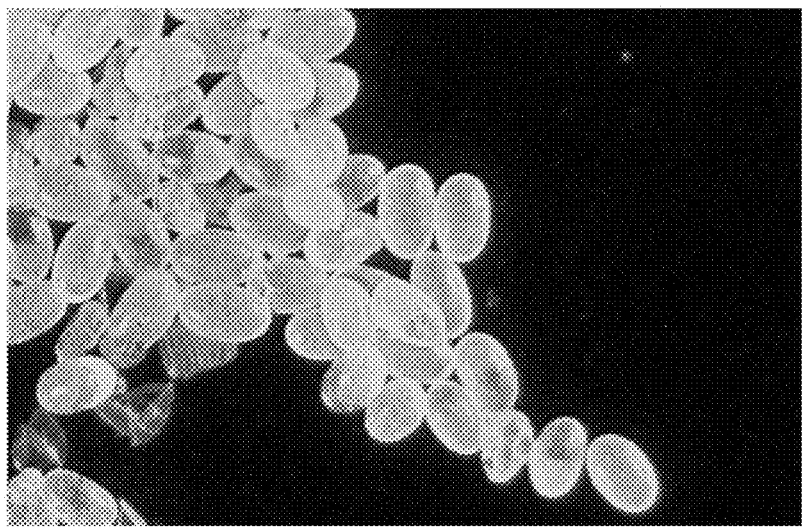
FIG. 5: *A. ovatus* eggs (A) and all stages of *A. ovatus* (B) after two months of cold storage and then one week at ambient temperature (eggs are in mean 132.5 μm long and 86.2 μm large). (A)
Figure 5:

Results are given FIG. 5.

Conclusion: These results show that sub-lethal astigmatid mite eggs do not develop fungus, and therefore do not deteriorate as fast as populations comprising all stages of astigmatid mites that had been stored in the same conditions.

Example 5: Specific Temperature Exposure and Duration of Exposure to Such Temperature Lead to Sub-Lethal Eggs Eggs of *A. ovatus* were isolated from a lab population and stored at different temperatures in an experimental cell (30 eggs/cell/treatment) for 4, 5 or 6 weeks

−5° C.

0° C.

8° C.

After storage, all eggs were put back to 25° C. and 75% HR conditions.

Every day during a week, every hatched or collapsed egg was noted, resulting in egg hatching, collapsing and edible rates.

Results are represented Table 1.

TABLE 1

*A. ovatus* egg collapsing and hatching rates depending on the storage temperature and on storage time.

| Exposure time | Treatment | Collapsing (A) | Hatching (B) | Edible (1 − A − B) |
|---|---|---|---|---|
| 4 weeks | −5° C. | 43.3% | 0% | 56.7% |
|  | 0° C. | 32.3% | 3.2% | 64.5% |
|  | 8° C. | 60% | 23.3% | 16.7% |

TABLE 1-continued

*A. ovatus* egg collapsing and hatching rates depending on the storage temperature and on storage time.

| Exposure time | Treatment | Collapsing (A) | Hatching (B) | Edible (1 − A − B) |
|---|---|---|---|---|
| 5 weeks | −5° C. | 56.7% | 0% | 43.3% |
|  | 0° C. | 13.3% | 0% | 86.7% |
|  | 8° C. | 61.3% | 29% | 9.7% |
| 6 weeks | −5° C. | 100% | 0% | 0% |
|  | 0° C. | 40% | 0% | 60% |
|  | 8° C. | 36.6% | 56.7% | 6.7% |

Storage at 0° C. provokes a massive egg's collapse and no hatching.
Storage at 8° C. still induces hatching and a high collapsing rate.
Storage at 0° C. conserves the egg turgescence, and reduces hatchability to zero after 5 week of exposure.

Conclusion: Astigmatid mites eggs exposed to a temperature of 0° C. for 4 to 6 weeks do not hatch, proving that the obtained eggs are sub-lethal eggs. Moreover, in those conditions, collapsing is minimized and it is possible to obtain more than 60% edible eggs.

The invention claimed is:

1. A method of rearing a population of arthropod biological control agents wherein the control agents are predators selected from the family Phytoseiidae, comprising feeding an effective amount of a nutrient source to the population of arthropod biological control agents, wherein the nutrient source comprises astigmatid mite eggs selected from eggs of *Acarus farris, Acarus immobilis, Acarus chaetoxysilos, Tyrophagus longior, Tyrophagus similis, Lardoglyphus konoi, Caloglyphus mycophagus, Caloglyphus berlesei, Suidasia nesbitti, Carpoglyphus munroi, Glycyphagus domesticus, Lepidoglyphus destructor, Blomia freemani,* or *Chortoglyphus arcuatus*, and wherein the nutrient source does not contain larvae, nymphs or adult astigmatid mites.

2. The method of claim 1, wherein the population of arthropod biological control agents comprises at least the species *Amblyseius swirskii*.

3. The method according toof claim 1, wherein the astigmatid mite eggs represent at least 10%, 20%, 25%, 30%, 35%, 40%, 45%, 50%, 55%, 60%, 65%, 70%, 75%, 80%, 85%, 90%, 95%, 98%, 100% by weight in relation to the total weight of the nutrient source.

4. The method of claim 1 wherein the arthropods and the astigmatid mite eggs are combined in a weight ratio between 1:3 and 1:7.

5. The method of claim 1 wherein the nutrient source further includes eggs of at least one lepidopteran species.

6. The method of claim 5 wherein the lepidopteran eggs are *Ephestia kuhniella* eggs.

7. The method of claim 5 wherein the lepidopteran eggs are *Sitotroga cerealella* eggs.

8. The method of claim 1 wherein the population of arthropod biological control agents includes arthropods within the genus *Amblyseius, Neoseiulus* or *Typhlodromips*.

9. The method of claim 1 wherein the population of arthropod biological control agents includes arthropods within the genus Amblyseius.

* * * * *